(12) United States Patent
Sakaguchi

(10) Patent No.: US 12,176,110 B2
(45) Date of Patent: Dec. 24, 2024

(54) LEARNING SUPPORT SYSTEM AND LEARNING SUPPORT METHOD

(71) Applicant: OLYMPUS CORPORATION, Tokyo (JP)

(72) Inventor: Seiichiro Sakaguchi, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 374 days.

(21) Appl. No.: 17/719,575

(22) Filed: Apr. 13, 2022

(65) Prior Publication Data
US 2022/0246303 A1 Aug. 4, 2022

Related U.S. Application Data

(63) Continuation of application No. PCT/JP2019/040875, filed on Oct. 17, 2019.

(51) Int. Cl.
*G06T 7/00* (2017.01)
*G06N 3/045* (2023.01)
(Continued)

(52) U.S. Cl.
CPC ............. *G16H 50/20* (2018.01); *G06N 3/045* (2023.01); *G06T 7/0012* (2013.01); *G16H 30/40* (2018.01);
(Continued)

(58) Field of Classification Search
CPC .................. G06T 7/00; G06T 7/0012; G06T 2207/10068; G06T 2207/20084;
(Continued)

(56) References Cited

U.S. PATENT DOCUMENTS 10,366,204 B2   7/2019  Tanner, Jr. et al.
10,810,461 B2 * 10/2020  Sugiura ................ G06V 40/172
(Continued)

FOREIGN PATENT DOCUMENTS

JP   2016087370 A   5/2016
JP   2018533103 A   11/2018
(Continued)

OTHER PUBLICATIONS

International Search Report dated Dec. 24, 2019 issued in PCT/JP2019/040875.
English Abstract of WO 2017/024071 A1, dated Feb. 9, 2017.
(Continued)

*Primary Examiner* — Tuan H Nguyen
(74) *Attorney, Agent, or Firm* — Scully, Scott, Murphy & Presser, P.C.

(57) ABSTRACT

A learning support system includes a storage configured to store an endoscope image and an annotation image generated in a first network, a processor acquiring the annotation image from the storage, using the annotation image to perform machine learning, and generating a trained model, and a server system performing communications with the processor, and being uploaded with a trained model. The storage and the processor each serve as a node constituting the first network, which is an intra-hospital network. The server system serves as a node constituting a second network, which is an extra-hospital network.

14 Claims, 12 Drawing Sheets

(51) Int. Cl.
  *G16H 30/40* (2018.01)
  *G16H 40/20* (2018.01)
  *G16H 50/20* (2018.01)

(52) U.S. Cl.
  CPC ... *G16H 40/20* (2018.01); *G06T 2207/10068* (2013.01); *G06T 2207/20081* (2013.01); *G06T 2207/20084* (2013.01)

(58) Field of Classification Search
  CPC .......... G06T 2207/20081; G16H 30/40; G16H 50/20; G16H 40/20; G06N 3/04; G06N 3/045; G06N 3/0454

See application file for complete search history.

(56) References Cited

U.S. PATENT DOCUMENTS

2018/0263568 A1* 9/2018 Yi .......................... A61B 5/202
2020/0218980 A1  7/2020 Matsumoto

FOREIGN PATENT DOCUMENTS

| JP | 2019139386 A | 8/2019 |
| WO | 2018142764 A1 | 8/2018 |
| WO | 2019069629 A1 | 4/2019 |

OTHER PUBLICATIONS

Kawakami, Akihisa, "Practice AWS! The design pattern of corporate cloud", Nikkei systems (Jan. 14, 2019), No. 310, pp. 54-61, with partial translation.

* cited by examiner

LEARNING SUPPORT SYSTEM AND LEARNING SUPPORT METHOD

CROSS REFERENCE TO RELATED APPLICATION

This application is a continuation of International Patent Application No. PCT/JP2019/040875, having an international filing date of Oct. 17, 2019, which designated the United States, the entirety of which is incorporated herein by reference.

BACKGROUND

A method of generating a trained model using an endoscope image captured using an endoscope system has been conventionally known. For example, Japanese Unexamined Patent Application Publication No. 2016-87370 discloses a method of performing machine learning based on an endoscope image, which is a captured image of the mucosa of the large intestine, generating a trained model, and classifying a pit pattern of a polyp of the large intestine based on the trained model.

In a conventional method of Japanese Unexamined Patent Application Publication No. 2016-87370 and the like, an endoscope image used for machine learning and an annotation image provided with information for identifying a region of interest are accumulated in a data server, and the trained model is generated using data accumulated in the data server. The data server mentioned herein is, for example, a server of a manufacturer of the endoscope system, and serves as a node constituting an external network outside a hospital that acquires the endoscope image and the like.

SUMMARY

In accordance with one of some aspect, there is provided a learning support system comprising: a storage configured to store an endoscope image generated in a first network and an annotation image generated in the first network, the annotation image having undergone annotation on a region of interest in the endoscope image; a processor including hardware, and a server system performing communications with the processor, and being uploaded with a trained model, wherein the processor acquires the annotation image from the storage, uses the annotation image to perform machine learning, and generates the trained model, the server system performs communications with the processor, and is uploaded with the trained model, the storage and the processor each serve as a node constituting the first network, the server system serves as a node constituting a second network, the first network is an intra-hospital network, and the second network is an extra-hospital network.

In accordance with one of some aspect, there is provided a learning support system comprising: a storage configured to store an endoscope image generated in a first network and an annotation image generated in the first network, the annotation image having undergone annotation on a region of interest in the endoscope image; and a processor including hardware, wherein the processor acquires the annotation image from the storage, uses the annotation image to perform machine learning, generates a trained model, and uploads the generated trained model to a server system, the storage and the processor each serve as a node constituting the first network, the server system serves as a node constituting a second network, the first network is an intra-hospital network, and the second network is an extra-hospital network.

In accordance with one of some aspect, there is provided a learning support system comprising a support processor including hardware and configured to perform communications with a processor to support machine learning, wherein the processor acquires an annotation image, from a storage that stores an endoscope image generated in a first network and the annotation image generated in the first network, the annotation image having undergone annotation on a region of interest in the endoscope image, uses the annotation image to perform the machine learning, generates a trained model, and uploads the generated trained model to a server system, the support processor selects a container including a model serving as an algorithm used for the machine learning and a framework serving as an execution environment for the machine learning in accordance with the model to support the machine learning, the storage and the processor each serve as a node constituting the first network, the server system serves as a node constituting a second network, the support processor serves as a node constituting a fourth network, the first network is an intra-hospital network, the second network is an extra-hospital network, and the fourth network is a network of a manufacturer of an endoscope system that generates the endoscope image.

In accordance with one of some aspect, there is provided a learning support method comprising: storing an endoscope image generated in a first network and an annotation image generated in the first network, the annotation image having undergone annotation on a region of interest in the endoscope image; using the annotation image to perform machine learning, and generating a trained model; and uploading the generated trained model to a server system that serves as a node constituting a second network, wherein each of the storing of the annotation image and the generation of the trained model is executed in the first network, the first network is an intra-hospital network, and the second network is an extra-hospital network.

DESCRIPTION OF EXEMPLARY EMBODIMENTS

Figure 1:
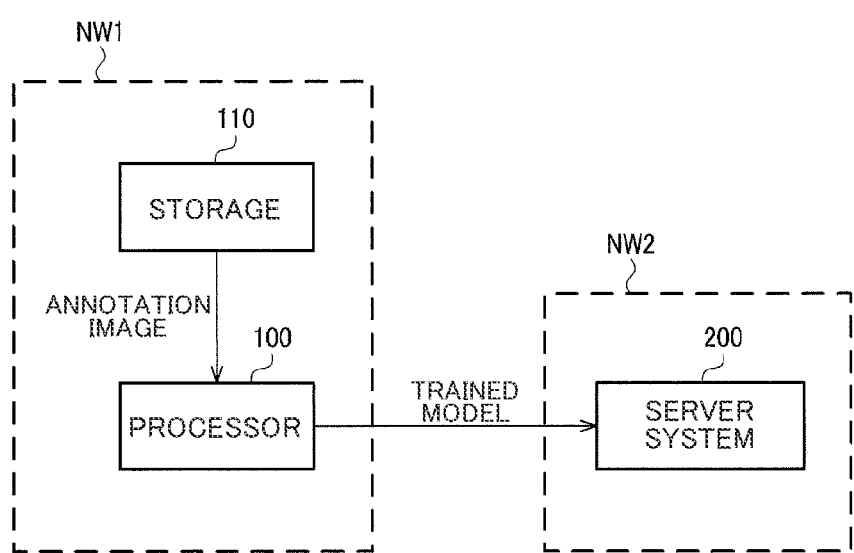
FIG. 1 illustrates a configuration example of a learning support system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. System Configuration Example

First, a description is given of a configuration example of a learning support system in accordance with the present embodiment. An overview of the system is described with reference to FIGS. 1 and 2, and a specific example of each network is described with reference to FIGS. 3 to 6.

1.1 Overall Configuration

A trained model using an endoscope image is conventionally generated by, for example, a manufacturer of an endoscope system. The manufacturer is provided by a hospital with an annotation image that is the endoscope image provided with an annotation, and performs learning processing using the annotation image as training data to generate the trained model. The annotation mentioned herein is data provided to the endoscope image, and is, specifically, information for identifying a position or the like of a region of interest in the endoscope image. The region of interest mentioned herein represents a region where an order of priority in observation for a user is relatively higher than that in other regions, and is, for example, a region that shows a mucosal site or a lesion in a case where the user is a doctor and wants to perform treatment. As another example, if a target that the doctor wants to observe is bubbles or feces, the region of interest is a region that shows a bubble portion or a feces portion. A target to which the user should pay attention is different depending on an observation purpose, but in any case, on the occasion of the observation, a region where the order of priority in observation for the user is relatively higher than that in other regions is the region of interest.

In addition, the manufacturer installs the trained model in their own endoscope system to implement an endoscope system capable of executing inference processing using the trained model. For example, an endoscope image captured in the endoscope system is input to the trained model, whereby a result of detection of the region of interest is output, similarly to an example described later with reference to FIG. 12. Presenting the result of detection to the doctor as the user enables appropriate support for the doctor's diagnosis or treatment.

However, in the conventional method, an endoscope image acquired at a given hospital and an annotation image that is the endoscope image provided with an annotation are leaked to an extra-hospital network. Since the endoscope image and the annotation image are information including a patient's privacy and are highly confidential, the exit of the endoscope image and annotation image from the hospital is not favorable in terms of security.

Additionally, processing of providing the endoscope image with an annotation is hard to be executed unless by a doctor who has expert knowledge. In generation of the trained model, as an amount of training data becomes larger, the accuracy is expected to be higher. Thus, there is a case where the number of endoscope images serving as a target of annotation becomes enormous, such as several tens of thousands or more. As described later with reference to FIG. 8B, in a such a case of providing the region of interest with a rectangular frame, a burden of providing one annotation is not so heavy. However, in a case where the enormous number of images are targeted as described above, a burden on the doctor becomes heavier. Additionally, as described later with reference to FIG. 8C, in a case where mask data in which the region of interest is solidly filled is provided as an annotation, it is necessary to consider where the region of interest starts and ends, which increases the burden on the doctor. Furthermore, there is also a case where even the doctor is hard to grasp a correct answer for where the region of interest starts and ends.

In this manner, the burden on the doctor when providing an annotation is heavy. Nonetheless, since the conventional method takes a form in which a hospital provides the manufacturer or the like playing a leading role in generating the trained model with endoscope images and annotation images, there is little return for individual doctors. In a case where the doctor utilizes the generated trained model, the trained model needs to be purchased from the manufacturer or the like. Since determination on what kind of the trained model is to be generated is made by the manufacturer or the like, there is a case where the trained model required by the doctor cannot be generated in the first place.

As described above, in accordance with the conventional method, despite the heavy burden on the doctor, a sufficient return for the burden is not provided in stages of generating and utilizing the trained model. Under such a situation, there is a possibility that the doctor is discouraged from cooperating in generation of the trained model, which has an adverse effect on development of the machine learning in the endoscope field.

FIG. 1 is a diagram illustrating a configuration of a learning support system in accordance with the present embodiment. As illustrated in FIG. 1, the learning support system includes a storage 110, a processor 100, and a server system 200. The storage 110 stores an endoscope image generated in a first network NW1 and an annotation image generated in the first network and having undergone annotation on the region of interest in the endoscope image. The processor 100 acquires the annotation image from the storage 110, uses the annotation image to perform machine learning, and generates the trained model. The storage 110 and the processor 100 each serve as a node constituting the first network NW1.

The processor 100 comprises hardware. The hardware can include at least one of a digital signal processing circuit or an analog signal processing circuit. For example, the hardware can be configured by one or more circuit devices mounted on a circuit board, or one or more circuit elements. The one or more circuit devices are, for example, integrated circuits (ICs) or the like. The one or more circuit elements are, for example, resistors, capacitors, or the like.

The processor 100 operates based on information stored in a memory. The memory mentioned herein may be the storage 110, or another memory that is not illustrated. The information is, for example, a program and various kinds of data or the like. The processor reads out a learning program for executing processing, which will be described later with reference to FIG. 7, for example, from the memory, executes the processing in accordance with the learning program, and thereby performs machine learning using the annotation image. The processor 100 outputs the trained model as a result of the machine learning.

The processor 100 may be, for example, a central processing unit (CPU). Note that the processor 100 is not limited to the CPU, and can be any of various other processors such as a graphics processing unit (GPU) and a digital signal processor (DSP). The above-mentioned memory may be a semiconductor memory such as a static random-access memory (SRAM) and a dynamic random-access memory (DRAM), or may be a register. The memory may also be a magnetic storage device such as a hard disk device, or may be an optical storage device such as an optical disk device. For example, the memory stores a computer-readable instruction, and the instruction is executed by the processor 100, whereby a function of the processor 100 is implemented as processing. The instruction mentioned herein may be an instruction set that is included in the program, or may be an instruction that instructs the hardware circuit included in the processor 100 to operate.

The storage 110 is preferably a hard disk device or a non-volatile memory such as a solid-state drive (SSD) in consideration of an enormous amount of image data to hold. However, the storage 110 is not limited thereto, and a storage device in another method may be used as the storage 110.

The server system 200 performs communications with the processor 100, and is uploaded with the trained model. The server system 200 serves as a node constituting a second network NW2. The server system 200 mentioned herein is not limited to one server, and may include a plurality of servers.

The first network NW1 is an intra-hospital network, and the second network NW2 is an extra-hospital network. The intra-hospital network is a private network constructed inside the given hospital, and is, for example, an intranet. The private network is a network capable of controlling a degree of disclosure to the outside (in a more limited sense, capable of keeping information undisclosed). Note that the number of hospitals included in the intra-hospital network is not limited to one, and a plurality of hospitals that manages highly confidential information in cooperation may be included. That is, the intra-hospital network may be one private network, or may be an aggregate of a plurality of private networks that can work together in managing highly confidential information. Details of the intra-hospital network will be described later with reference to FIGS. 3, 4, 5A, and 5B. The intra-hospital network is a network outside the intra-hospital network, and is, for example, a public telecommunication network such as the Internet.

In a method in accordance with the present embodiment, the endoscope image and the annotation image are acquired and accumulated in the first network NW1, and the trained model is generated in the processor 100 of the first network NW1. Information output from the first network NW1 to the second network NW2, which is an external network, is the trained model. The endoscope image and the annotation image used for generation of the trained model cannot be identified from the trained model. The method in accordance with the present embodiment eliminates the need for transmitting the endoscope image and the annotation image to the outside of the intra-hospital network, and thereby enables management of highly confidential information in a more secure state.

Additionally, in the method in accordance with the present embodiment, machine learning is performed using the processor 100 in the intra-hospital network. Since staff associated with the hospital such as a doctor play the leading role in generating the trained model, it is possible to generate a highly needed trained model and use the trained model in a free form. As described above, transmitting the trained model to the outside of the intra-hospital network poses little problem in terms of security. For this reason, it is also possible to receive remuneration by making the generated trained model available to others. With an increased advantage of getting involved in generation of the trained model for the doctor, it is possible to expedite the machine learning in the endoscope field.

Figure 2:
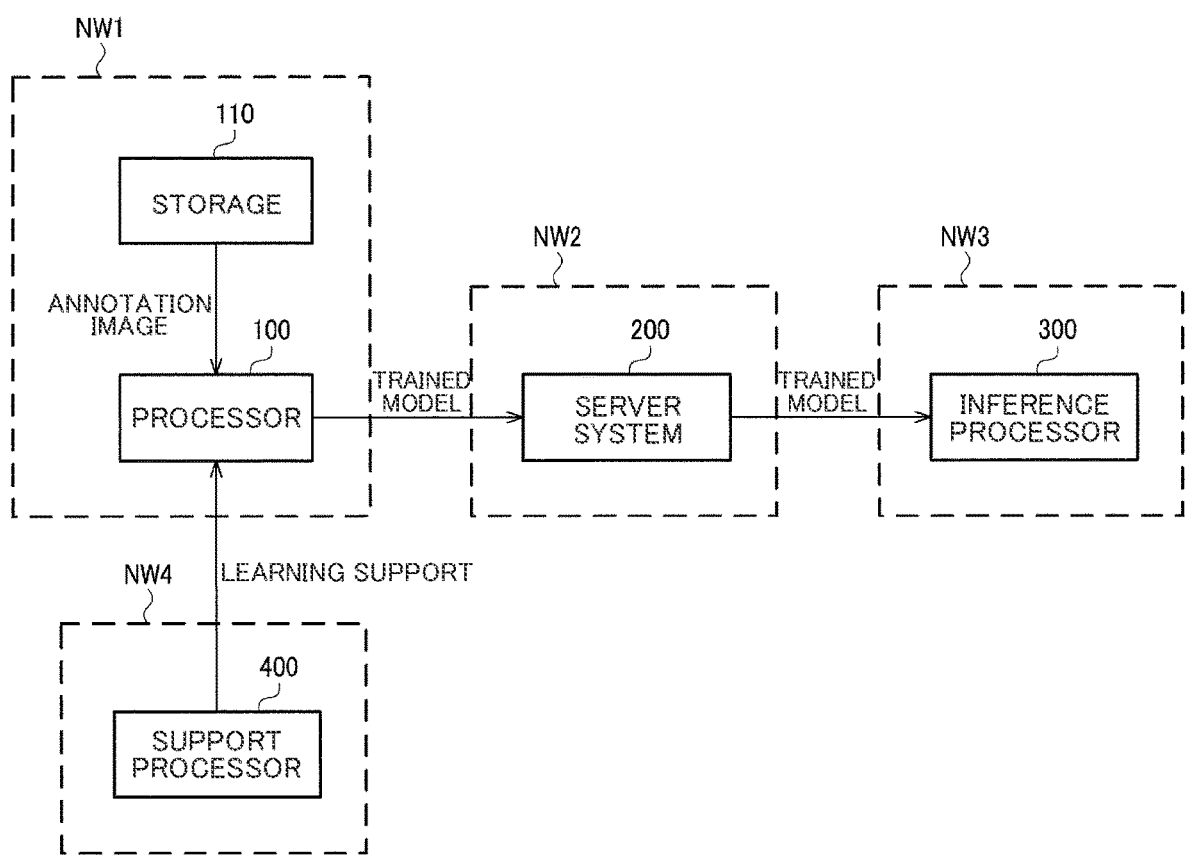
FIG. 2 illustrates a detailed configuration example of the learning support system.

FIG. 2 illustrates another configuration example of the learning support system in accordance with the present embodiment. The storage 110, the processor 100, the server system 200, the first network NW1, and the second network NW2 are similar to those illustrated in FIG. 1.

The learning support system may include an inference processor 300, in addition to the storage 110, the processor 100, and the server system 200. The inference processor 300 performs communications with the server system 200 to download the trained model, and performs detection processing of detecting the region of interest from an inference endoscope image based on the trained model. The detection processing mentioned herein includes processing of determining whether or not the region of interest exists in the inference endoscope image, processing of identifying a position of the region of interest in the inference endoscope image, and processing of identifying the position and shape of the region of interest in the inference endoscope image. In a case of detecting a plurality of types of regions of interest, the detection processing mentioned herein includes classification processing of classifying the region of interests.

In a case where the region of interest is a lesion in the mucosa, the classification processing may be such processing as to discriminate whether or not the lesion as a result of detection is cancer. For example, in a case of binary classification of cancer/non-cancer, a probability of cancer is displayed next to the region of interest.

Alternatively, the detection processing may be scene recognition processing. In this case, classification into about ten classes is performed in accordance with a scene such as a water supply scene, a white light observation scene, and a narrow band imaging (NBI) observation scene.

Still alternatively, the detection processing may be processing of dividing a region seen on a screen. For example, whether or not the region of interest corresponds to a specific organ (the liver, the gallbladder, the common bile duct, or the like in a case of laparoscopic cholecystectomy) is classified on a pixel-by-pixel basis.

Furthermore, a function of tracking the region of interest detected in the detection processing with high accuracy may be added. For example, in a case of tracking the region of interest in a movie, it is possible to keep capturing the region of interest at lower cost than that in a case of performing the detection processing every time on still images in each frame. Additionally, the region of interest over a plurality of frames can be recognized as "one region of interest".

The inference processor 300 serves as a node constituting a third network NW3, and the third network NW 3 is a network of the inference hospital as a hospital that executes the inference processing. The inference endoscope image is an image serving as an input of the inference processing using the trained model, and is, specifically, an image captured using the endoscope system serving as the node of the third network NW3.

This enables utilization of the trained model generated in the first network NW1, which is a given intra-hospital network, in the third network NW3, which is an intra-hospital network of another hospital. Details of the third network NW3 will be described later with reference to FIG. 6. Through the intervention of the server system 200, it is possible to smoothly provide and utilize the trained model. Since the utilization of the generated trained model is expedited, there is an advantage for a trained model generation side in easiness of receiving remuneration. Since it is possible to select one that suits own need from a plurality of trained models generated by various hospitals, there is an advantage for a trained model utilization side in increased convenience.

Note that the following description will be given of an example in which the trained model is generated in the first network NW1, and the trained model is utilized in the third network NW3. For this reason, a hospital in which the first network NW1 is constructed is represented by a learning hospital, and a hospital in which the third network NW3 is constructed is represented by an inference hospital. Note that each hospital is not limited to a hospital that performs either generation or utilization of the trained model. For example, in the intra-hospital network of each hospital, both processing of generating the trained model by itself and processing of acquiring the trained model generated by others and utilizing the trained model may be performed. That is, focusing on one trained model, the inference processor 300 mentioned herein is a processor that downloads the trained model from the server system 200 to perform the inference processing, and the inference hospital represents a hospital in which a network including the inference processor 300 as a node is constructed. Thus, a possibility that the inference hospital with respect to a certain trained model serves as the learning hospital with respect of another trained model is not precluded.

In recent years, commoditization of artificial intelligence (AI) has advanced. Specifically, a multitude of models and frameworks, which will be described later with reference to FIG. 10, have been disclosed, and many of them can be freely used. Hence, even a doctor who is not an expert in AI has become able to generate the trained model by combining the models and the frameworks. However, there is a case where learning cannot be performed appropriately depending on a combination of a model and a framework, and there is also a case where a result of learning does not converge depending on a setting of a learning parameter. In consideration of this point, learning support by a support processor 400 may be performed.

The learning support system further includes the support processor 400 that performs communications with the processor 100 to support the machine learning, as illustrated in FIG. 2. The support processor 400 serves as a node constituting a fourth network NW4, and the fourth network NW4 is a network of a manufacturer of the endoscope system used for generation of the endoscope image in the first network NW1.

Installing the trained model in the endoscope system can increase accuracy of the processing of detecting the region of interest from the endoscope image and classifying the region of interest. For this reason, it is highly likely that the manufacturer of the endoscope system generates the trained model and attempts to enhance a function of the endoscope system using the trained model. That is, the manufacturer of the endoscope system has a higher degree of expertise regarding generation of the trained model. In addition, since the manufacturer also designs an optical system of the endoscope system and an image processing program, there is a high probability that the manufacturer has knowledge about characteristics such as brightness, hue, and the like of the endoscope image, a learning method appropriate for the endoscope image, and other information. Hence, the manufacturer of the endoscope system performs learning support using the support processor 400, and can thereby perform the machine learning using the endoscope image smoothly.

Note that the fourth network NW4 including the support processor 400 is a network outside the first network NW1 as the intra-hospital network. For this reason, if the endoscope image or the annotation image is transmitted to the support processor 400 in a freely available form, there is a possibility of undermining effects of protecting highly confidential information by the method in accordance with the present embodiment. Hence, the learning support by the support processor 400 is preferably support in a form in which the endoscope image and the annotation image are not browsed, or support in a form in which the endoscope image and the annotation image are provided in a state where secondary utilization is not permitted. Details of the learning support using the support processor 400 will be described later with reference to FIG. 10.

As the learning support system in accordance with the present embodiment, the description has been given of the example including the storage 110, the processor 100, and the server system 200, and the example including the inference processor 300 or the support processor 400 in addition to the storage 110, the processor 100, and the server system 200. Note that the learning support system may include both the inference processor 300 and the support processor 400. However, the learning support system in accordance with the present embodiment is not limited thereto.

For example, the method in accordance with the present embodiment can be applied to a learning support system including the storage 110 and the processor 100. The storage 110 stores the endoscope image generated in the first network NW1 and the annotation image generated in the first network NW1 and having undergone annotation on the region of interest in the endoscope image. The processor 100 acquires the annotation image from the storage 110, uses the annotation image to perform the machine learning, generates the trained model, and uploads the generated trained model to a server system. As described above, the storage 110 and the processor 100 each serve as the node constituting the first network NW1, and the server system 200 serves as the node constituting the second network NW2. The first network NW1 is the intra-hospital network, and the second network NW2 is the extra-hospital network.

Additionally, the method in accordance with the present embodiment can be applied to a learning support system including the support processor 400. The support processor 400 performs communications with the processor 100 to support the machine learning. The support processor 400 acquires, from the storage 110 that stores the endoscope image generated in the first network NW1 and the annotation image generated in the first network NW1 and having undergone annotation on the region of interest in the endoscope image, the annotation image, uses the annotation image to perform the machine learning, generates the trained model, and uploads the generated trained model to the server system 200. The support processor 400, as described later with reference to FIG. 10, selects a container includes a model serving as an algorithm used for the machine learning and a framework serving as an execution environment for the machine learning in accordance with the model to support the machine learning. The storage 110 and the processor 100 each serve as the node constituting the first network NW1, the server system 200 serves as the node constituting the second network NW2, and the support processor 400 serves as the node constituting the fourth network NW4. The first network NW1 is the intra-hospital network, the second network NW2 is the extra-hospital network, and the fourth network NW4 is the network of the manufacturer of the endoscope system that generates the endoscope image.

Additionally, the method in accordance with the present embodiment can be applied to a learning support method of executing processing in the learning support system. The learning support method includes storing the endoscope image generated in the first network NW1 and the annotation image generated in the first network NW1 and having undergone annotation on the region of interest in the endoscope image, using the annotation image to perform the machine learning, generating the trained model, and uploading the generated trained model to the server system serving as the node constituting the second network NW2. Each of the storing of the annotation image and the generation of the trained model is executed in the first network NW1. The first network NW1 is the intra-hospital network, and the second network is the extra-hospital network.

1.2 Intra-Hospital Network

Figure 3:
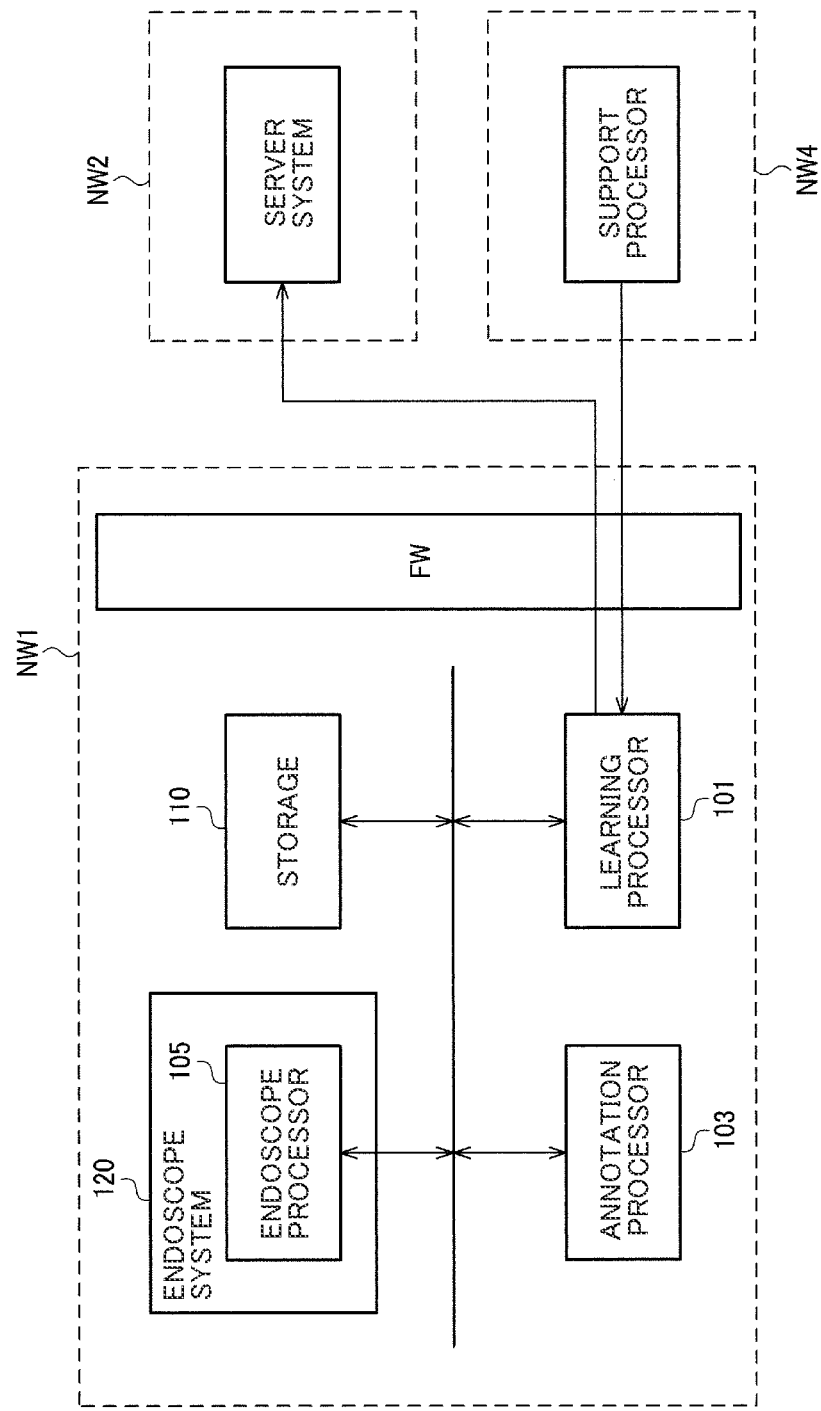
FIG. 3 illustrates a configuration example of a first network as an intra-hospital network.

Subsequently, a specific example of the intra-hospital network is described. FIG. 3 illustrates a specific example of nodes constituting the intra-hospital network, and is a diagram for describing connection with the other networks. As illustrated in FIG. 3, the first network NW1 as the intra-hospital network includes an endoscope system 120, the storage 110, an annotation processor 103, and a learning processor 101 as nodes. Note that the nodes of the intra-hospital network are not limited to those illustrated in FIG. 3, and another node may be added.

Figure 4:
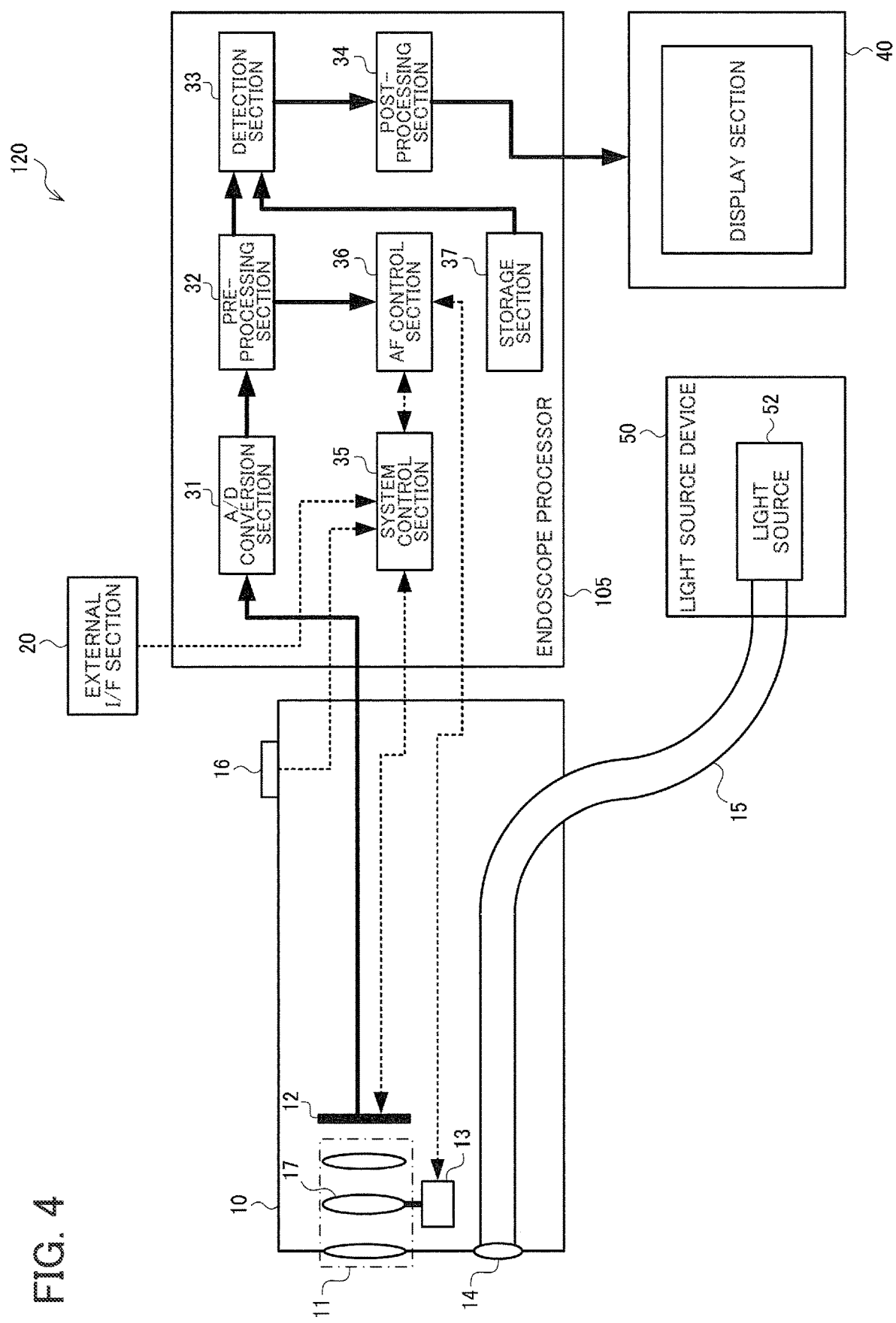
FIG. 4 illustrates a configuration example of an endoscope system.

FIG. 4 illustrates a configuration example of the endoscope system 120. The endoscope system 120 includes an insertion section 10, an external interface (I/F) section 20, an endoscope processor 105, a display section 40, and a light source device 50. Note that a configuration of the endoscope system 120 is not limited to that illustrated in FIG. 4. Various modification can be made such as omission of part of the configuration and addition of another constituent element. As the endoscope system 120, a flexible scope used for the digestive tract or the like, or a rigid scope used for a laparoscope or the like can be assumed, but the endoscope system 120 is not limited thereto.

The insertion section 10 is a portion that is inserted into the body. The insertion section 10 includes an objective optical system 11, an image sensor 12, an actuator 13, an illumination lens 14, a light guide 15, and an auto focus (AF) start/end button 16.

The light guide 15 guides light emitted from the light source 52 to a distal end of the insertion section 10. The illumination lens 14 emits illumination light guided by the light guide 15 onto a subject. The objective optical system 11 receives reflected light from the subject and forms an image as a subject image. The objective optical system 11 includes a focus lens 17, and is capable of changing a position at which a subject image is formed in accordance with a position of the focus lens 17. The actuator 13 drives the focus lens 17 based on an instruction from an AF control section 36. Note that AF is not essential, and the endoscope system 120 may have a configuration not including the AF control section 36.

The image sensor 12 receives light from the subject having passed through the objective optical system 11. The image sensor 12 may be a monochrome sensor, or may be a sensor having a color filter. The color filter may be a color filter in a well-known Bayer's arrangement, a complementary color filter, or another color filter. The complementary filter includes filters in respective colors of cyan, magenta, and yellow.

The AF start/end button 16 is an operation interface for a user to perform an operation of starting/ending the AF. The external I/F section 20 is an interface for the user to perform an input operation to the endoscope system 120. The external I/F section 20 includes, for example, a button for setting an AF control mode, a button for setting an AF region, and a button for adjusting an image processing parameter.

The endoscope processor 105 performs image processing and control of the whole system. Note that the endoscope processor 105 may be one processor, or may include a plurality of processors. For example, the endoscope processor 105 may include a CPU that performs control of the whole system and a GPU that performs image processing. The plurality of processors in this case may be arranged within one device, or may be arranged in different devices. The endoscope processor 105 includes an analog/digital (A/D) conversion section 31, a pre-processing section 32, a detection section 33, a post-processing section 34, a system control section 35, the AF control section 36, and a storage section 37.

The A/D conversion section 31 converts analog signals, which are sequentially output from the image sensor 12, into digital images, and sequentially outputs the digital images to the pre-processing section 32. The pre-processing section 32 performs various kinds of correction processing on captured images sequentially output from the A/D conversion section 31, and sequentially outputs the captured images to the detection section 33 and the AF control section 36. The correction processing includes, for example, white balance processing and noise reduction processing.

The detection section 33 operates in accordance with the trained model stored in the storage section 37 to perform detection processing of detecting the region of interest from the captured image. The endoscope system 120 utilized in the learning hospital is assumed herein as the detection section 33, and the trained model is generated in the learning hospital. Note that processing in the detection section 33 may be omitted in a stage before the trained model is generated. Alternatively, as described above, the trained model uploaded to the server system 200 by others may be downloaded and used. In a case where the trained model is a neural network, the detection section 33 performs arithmetic processing in a forward direction using a weight coefficient determined by learning performed with an image from the pre-processing section 32 serving as the inference endoscope image. The detection section 33 then outputs a result of detection of the region of interest based on an output from an output layer.

The post-processing section 34 performs post-processing based on the result of the detection processing in the detection section 33, and outputs an image having undergone the post-processing to the display section 40. As the post-processing mentioned herein, emphasizing processing that increases visibility of the region of interest in the inference endoscope image or other processing can be assumed.

The system control section 35 is connected to each of the image sensor 12, the AF start/end button 16, the external I/F section 20, and the AF control section 36, and controls each section. Specifically, the system control section 35 inputs/outputs various kinds of control signals. The AF control section 36 uses images sequentially output from the pre-processing section 32 to perform AF control.

The display section 40 sequentially displays images output from the post-processing section 34. The display section 40 is, for example, a liquid crystal display, an electroluminescence (EL) display, or the like. The light source device 50 includes a light source 52 that emits illumination light. The light source 52 may be a xenon light source, a light emitting diode (LED), or a laser light source. Alternatively, the light source 52 may be another light source, and a light emission method is not specifically limited.

An endoscope system of a hospital in which the inference processor 300 is installed may be similarly configured. Furthermore, an output from the inference processor 300 may be fed back to control of the endoscope system. Assuming that the detection processing is processing of classifying the region of interest, when a halation region is recognized, control to decrease an output of the light source is performed. Additionally, when a lesion is detected, control to prompt enlargement is performed.

Back to FIG. 3, the description about the intra-hospital network continues. The storage 110 is as described with reference to FIGS. 1 and 2, and acquires an image captured by the endoscope system 120 as the endoscope image. The endoscope image is, for example, an image output from the pre-processing section 32.

The annotation processor 103 provides the endoscope image captured by the endoscope system 120 with an annotation. Specifically, the annotation processor 103 accepts an input of an annotation made by a doctor or the like, and generates the annotation image based on the input. The annotation image mentioned herein is, for example, multidimensional image data in which the endoscope image and the annotation image (mask image) are associated with each other, as described later with reference to, for example, FIG. 8C. Details of processing in the annotation processor 103 will be described later. The generated annotation image is accumulated in the storage 110.

The learning processor 101 performs the machine learning based on the annotation image to generate the trained model. The learning processor 101 corresponds to the processor 100 illustrated in FIGS. 1 and 2. Note that the learning processor 101 and the annotation processor 103 may be different processors, or may be an identical processor. That is, the processor 100 of the learning support system may be a processor that performs both the machine learning in the learning processor 101 and the processing of generating the annotation image in the annotation processor 103. The first network NW1 may include another node that is not illustrated in FIG. 3. Additionally, the processor 100 of the learning support system may include a processor that is not illustrated.

The intra-hospital network is a more secure network for the endoscope image and the annotation image, as compared with the extra-hospital network. Security mentioned herein is, specifically, information security, and especially relates to confidentiality. The confidentiality is to make information unavailable or undisclosed to a non-permitted target. That is, being more secure represents a state where information is hard to be leaked as compared with a case of being less secure. Note that being more secure may also be referred to as being less vulnerable for the endoscope image and the annotation image. Limiting a location where communications for the endoscope image and the annotation image are performed to the inside of the first network NW1 as the intra-hospital network can prevent unauthorized leakage of highly confidential information.

For example, the intra-hospital network is a network that restricts accessible Internet Protocol (IP) addresses. In other words, the security in the present embodiment may be network security. As one example, the first network NW1 includes a fire wall FW that restricts access to a node in the first network NW1 from a node of an external network. Arranging the fire wall FW restricts access from the node belonging to the external network. For example, in a case of performing access control using the IP, the fire wall FW holds a list of IP addresses accessible to the intra-hospital network, and blocks access from an IP address not included in the list. Additionally, the fire wall FW may determine whether access is permitted or blocked depending on a combination of an IP address and a port number. Putting such access restriction enables management of the endoscope image and the annotation image in the intra-hospital network in a more secure form.

The first network NW1 serving as the intra-hospital network may be an intranet, and the second network serving as the extra-hospital network may be the Internet. Using the intranet, which is a closed network, can prevent unauthorized access from the outside of the first network NW1. Specifically, in the intranet, the above-mentioned fire wall FW is arranged in many cases, and access control using the fire wall FW can be performed.

Note that as illustrated in FIG. 3, access to the intra-hospital network from the outside is severely restricted, but access to the external server system 200 from a node of the intra-hospital network can be made. For example, the learning processor 101 may be permitted to make free access to an external node. This enables uploading to the server system 200, thereby expediting utilization of the generated trained model. However, there is also a case where the trained model is available only to specific other people, for example, clients who pay fees. To prevent transmission of the trained model to an inappropriate target, such access control as to limit a target to which the learning processor 101 is accessible to the server system 200 may be performed.

In addition, in a case where the support processor 400 is used, the fire wall FW permits access to a node in the intra-hospital network, specifically, the learning processor 101, from the support processor 400. However, as described above, configuring the support processor 400 to be capable of acquiring the endoscope image and the annotation image causes highly confidential information to be transmitted to the fourth network NW4 as the extra-hospital network, and thus is not favorable. Hence, it is preferable not to permit the support processor 400 to make access to the endoscope image and the annotation image, or to transmit the endoscope image and the annotation image with a read-only attribute. In this case, a user who uses the support processor 400, for example, an employee of the manufacturer of the endoscope system, can browse the endoscope image and the annotation image using a display section connected to the support processor 400. Note that the endoscope image and the annotation image are provided in a form in which the images cannot be stored. For this reason, in the learning support, secondary utilization of the endoscope image and the annotation image is not permitted in the support processor 400. The secondary utilization mentioned herein represents storing of the endoscope image and the annotation image, and utilization of the endoscope image and the annotation image for another intended use and transmission of the endoscope image and the annotation image to another node.

Additionally, the intra-hospital network in accordance with the present embodiment represents the intranet constructed within one hospital in a more limited sense. Note that cooperation of a plurality of hospitals enables effective execution of the machine learning.

For example, considering a case of a medical corporation that owns a plurality of hospitals, aggregation of endoscope images and annotation images acquired in the plurality of hospitals can increase an amount and types of training data used for the machine learning. Examples of the types mentioned herein include a type regarding a part as a target of image-capturing, a position or size of the region of interest, and brightness, saturation, or the like of an image. Hence, as compared with a case of performing the machine learning in a single hospital, it is possible to increase accuracy of the machine learning.

Alternatively, cooperation of a plurality of hospitals having different management agencies can be assumed. For example, endoscope images and annotation images are transmitted/received between the plurality of hospitals that has received approval as hospitals taking charge of part of research. In this case, since the plurality of hospitals having a more distant relationship than that of an identical medical corporation woks together, it can be assumed that types of endoscope images and annotation images become more diverse. For example, there is also a case where the endoscope system of one manufacturer is used in one hospital or the medical corporation, and thus there is a possibility for a bias in learning contents. From this point, cooperation of the plurality of hospitals having different management agencies allows endoscope images and annotation images captured by endoscope systems of different manufacturers to serve as training data, and thereby enables increased diversity of the generated trained model.

However, attention needs to be paid to connection between intranets constructed in the plurality of hospitals. In a case where connection between the intranets is established simply using a public telecommunication network such as the Internet, there is a risk in terms of security such as tapping and falsification. Although establishing connection between the intranets using a dedicated line can strengthen security, there is a disadvantage that cost of the dedicated line is high.

Figure 5A:
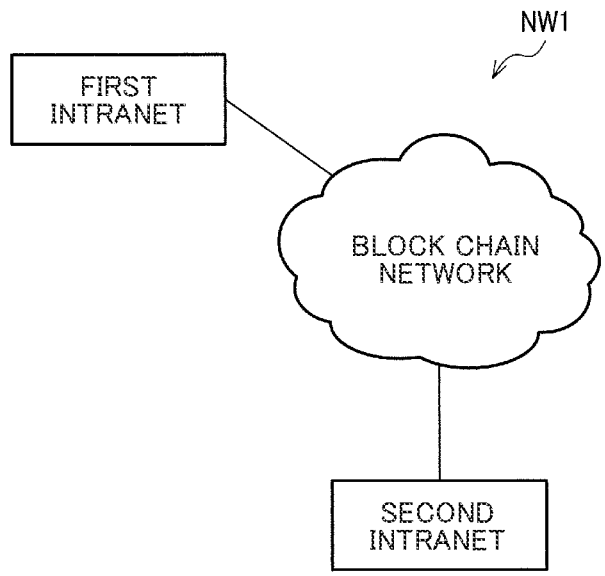
FIGS. 5A and 5B each illustrate the intra-hospital network including a plurality of intranets.
Figure 5B:
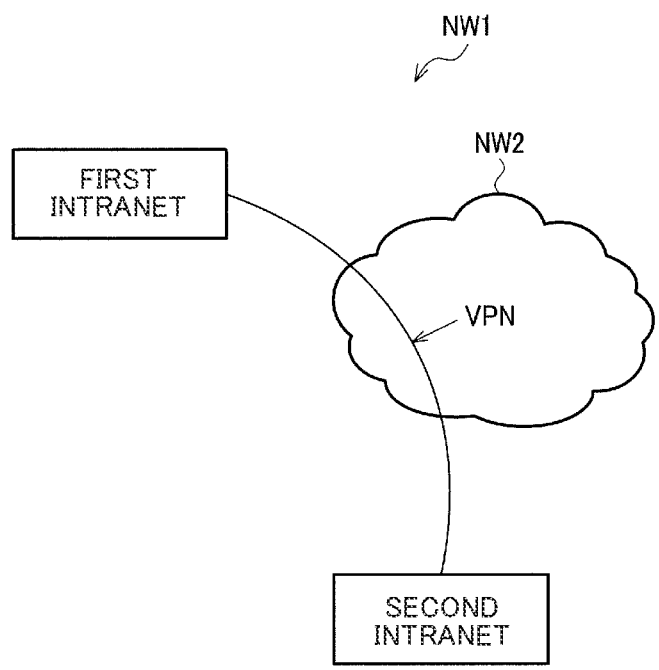

FIGS. 5A and 5B each illustrate a specific example of the intra-hospital network including a plurality of intranets. As illustrated in FIGS. 5A and 5B, the intra-hospital network may include a first intranet and a second intranet. In addition, intranets included in the intra-hospital network can be expanded to three or more intranets.

As illustrated in FIG. 5A, a given node in the first intranet and a given node in the second intranet are nodes constituting a block chain network. The block chain network mentioned herein represents a network using a block chain. The block chain network is, for example, a peer-to-peer (P2P) network that is implemented in the second network NW2, which is, for example, the Internet. In the block chain network, a data structure called the block chain in which a plurality of blocks is connected in a chained form is used.

A client application of the block chain is installed in the given node in the first intranet and the given node in the second intranet. The client application is software for participating in the block chain network. The client application is, for example, software for executing various kinds of processing performed in the block chain network, such as generation and issuance of a transaction, processing of a consensus algorithm, and management of a virtual currency.

The block chain employs various kinds of methods for preventing tapping and falsification such as encryption and addition of a block using the consensus algorithm. This increases security for data transmitted/received using the block chain network. Hence, for example, even in a case where the plurality of intranets is connected using the public telecommunication network such as the Internet, it is possible to construct a more secure intra-hospital network.

As illustrated in FIG. 5B, the first intranet and the second intranet may constitute a virtual private network (VPN). The VPN mentioned herein may be a VPN using the Internet, or a VPN using a closed network provided by a communication common carrier. In the VPN, performing communications by tunneling encrypted data enables prevention of falsification or the like of communication data. Hence, it is possible to connect the plurality of intranets and construct the more secure intra-hospital network.

Note that the endoscope image and the annotation image may be transmitted/received in plain texts within one intranet. In this regard, the annotation image or the like may be encrypted in communications between nodes of the intranet to further increase security.

1.3 Inference Hospital Network

Figure 6:
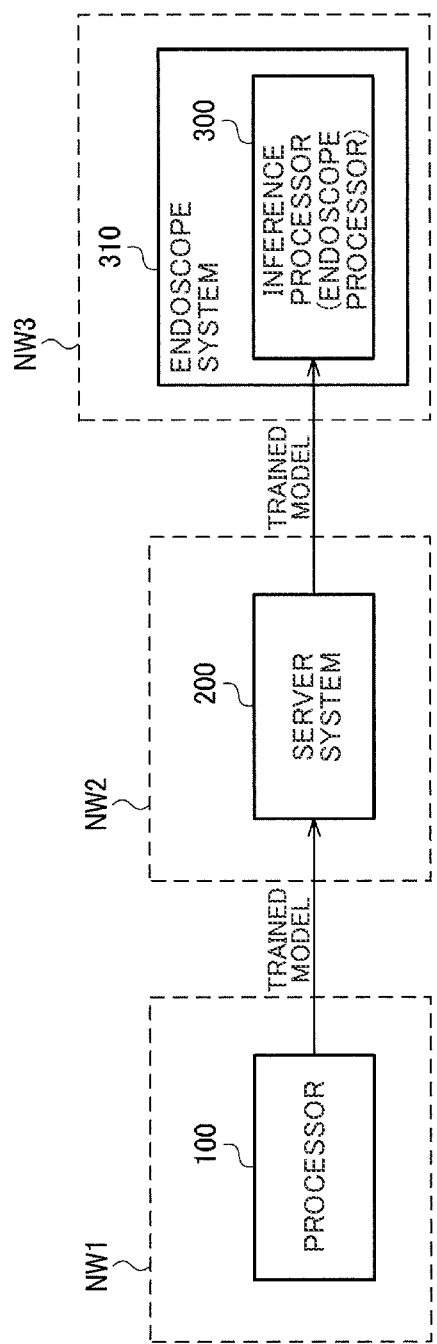
FIG. 6 illustrates a configuration example of a third network as a network of an inference hospital.

FIG. 6 is a diagram illustrating a specific example of the third network NW3 serving as a network of the inference hospital. As illustrated in FIG. 6, the third network NW3 includes an endoscope system 310, and the inference processor 300 may be a processor included in the endoscope system 310.

The endoscope system 310 mentioned herein is similar to the endoscope system 120 described above with reference to, for example, FIG. 4, and the inference processor 300 corresponds to the endoscope processor 105 illustrated in FIGS. 3 and 4. However, the endoscope system 120 of the learning hospital and the endoscope system 310 of the inference hospital may be an identical model, or may be different models. In addition, manufacturers of the endoscope systems are not necessarily matched, and the endoscope system 120 and the endoscope system 310 may be products of different manufacturers.

The endoscope system 310 includes a memory that stores the trained model downloaded from the server system 200. The inference processor 300 reads out the trained model from the memory, inputs an image captured by an image sensor to the trained model as the inference endoscope image, and thereby performs processing of detecting the region of interest from the inference endoscope image. In a case where the endoscope system 310 has a configuration similar to that illustrated in FIG. 4, the inference endoscope image is an image having undergone pre-processing. Additionally, the inference processor 300 performs processing corresponding to that of the detection section 33 illustrated in FIG. 4.

As described above, in the network of the inference hospital, the trained model acquired through the server system 200 is applied to the endoscope system serving as a node of the network. This facilitates utilization of the trained model generated by others, and enables detection of the region of interest with high accuracy using the trained model.

2. Learning Processing

Subsequently, details of the learning processing executed in the intra-hospital network of the learning hospital will be described. First, a description is given of the flow of the machine learning using a flowchart in FIG. 7, and thereafter a description is given of processing of generating the annotation image and specific learning processing.

2. 1 Flow of Machine Learning

Figure 7:
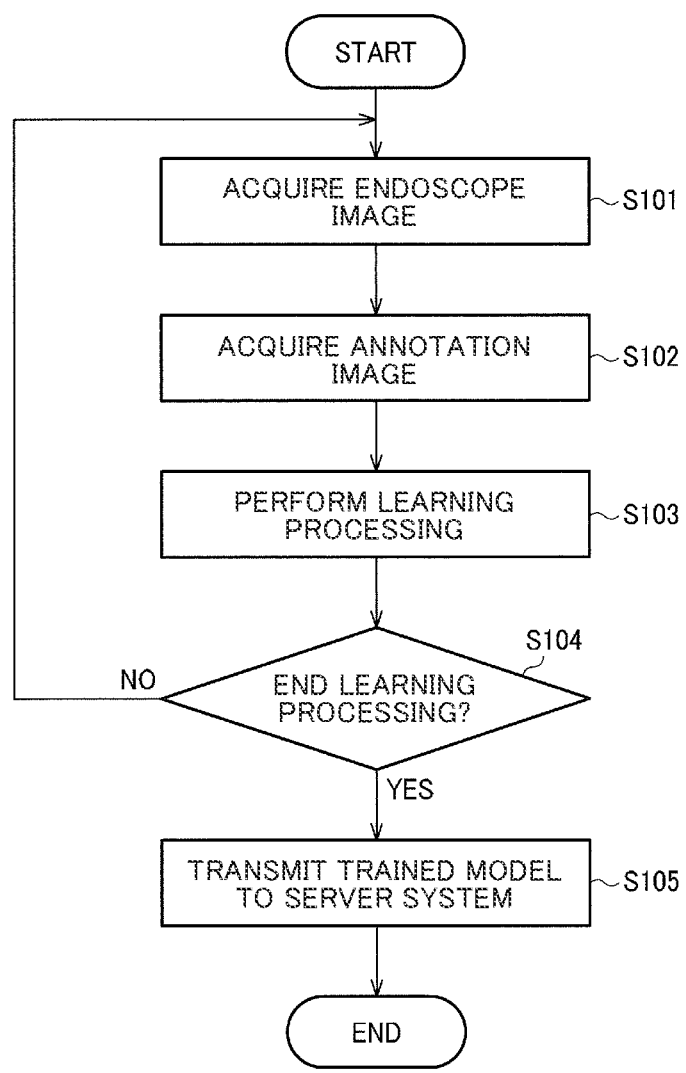
FIG. 7 is a flowchart describing learning processing.

FIG. 7 is a diagram for describing the learning processing executed by each processor serving as a node of the first network NW1. In the learning processing, the endoscope image is first acquired in step S101. Processing in step S101 is executed by the endoscope processor 105 to control the light source 52, the image sensor 12, and the like to capture an in-vivo image, and store a result of image-capturing in the storage 110.

In step S102, the annotation image is acquired. Processing in step S102 includes processing executed by the annotation processor 103 to read out the endoscope image from the storage 110, to cause the display section to display the readout endoscope image, to accept an input of an annotation from a user, and to store the accepted annotation in association with the endoscope image in the storage 110 as the annotation image.

In step S103, the learning processor 101 performs the machine learning based on the annotation image. For example, in a case where the neural network is used, processing in step S103 is to execute, based on the annotation image, each of the arithmetic processing in the forward direction, the processing of calculating the error function, and the processing of updating the weight coefficient based on the error function one time.

In step S104, the learning processor 101 determines whether or not to end the machine learning. For example, the learning processor 101 divides a multitude of data sets that has been acquired into training data and verification data. The learning processor 101 then performs processing using the verification data on the trained model acquired by performing the learning processing based on the training data to determine accuracy. Since the verification data is associated with a correct answer label corresponding to an annotation, the learning processor 101 can determine whether or not a result of detection based on the trained model is correct. Being correct mentioned herein represents that the result of detection is sufficiently close to the correct answer label. In a case where a percentage of correct answers to the verification data is equal to or greater than a predetermined threshold, the learning processor 101 determines end of learning (YES in step S104), and ends the machine learning. Alternatively, the learning processor 101 may determine the end of the learning when having executed the processing described in step S103 a predetermined number of times.

In step S105, the learning processor 101 performs processing of transmitting the generated trained model to the server system 200. Note that the learning processor 101 may perform processing of storing the trained model in the storage 110.

2. 2 Annotation

The processing of generating the annotation image executed in step S102 is now described. The annotation in accordance with the present embodiment represents provision of information for identifying a position or the like of the region of interest in the endoscope image and the provided information.

Figure 8C:
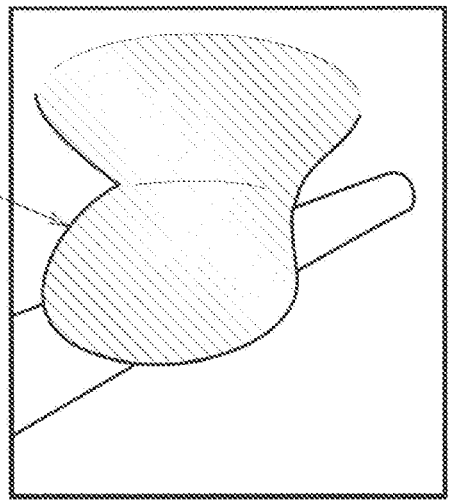
FIGS. 8B and 8C each illustrate an example of the endoscope image provided with an annotation.
Figure 8B:
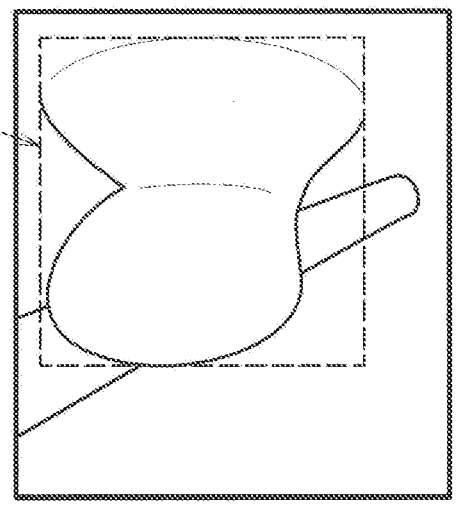
Figure 8A:
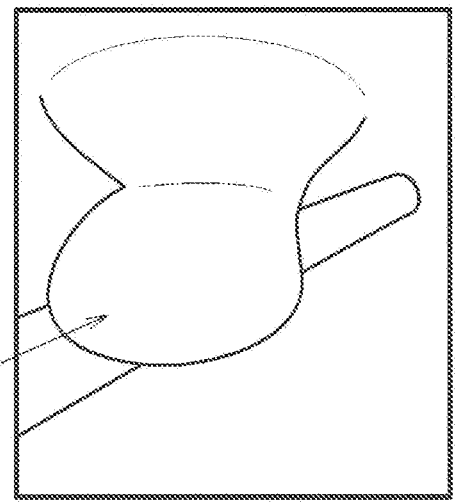
FIG. 8A illustrates an example of an endoscope image.

FIG. 8A illustrates the endoscope image. FIGS. 8B and 8C each illustrate the endoscope image provided with an annotation. As illustrated in FIG. 8A, an image of a target object OB, which is a polyp, is captured in the endoscope image. The region of interest mentioned herein is a region corresponding to the target object OB, out of the endoscope image. As illustrated in FIG. 8B, the annotation is, for example, information that identifies a rectangular region that contains the region of interest. In this case, the annotation is represented by four values composed of an x-coordinate and a y-coordinate indicating a vertex on an upper left side of the rectangular region, and an x-coordinate and a y-coordinate indicating a vertex on a lower right side of the rectangular region. An x-axis mentioned herein is an axis set in a lateral direction of an image, and a y-axis is an axis set in a vertical direction of the image. Note that the information that identifies the rectangular region may be a set of coordinate values of the vertex on the upper left side, a length in the vertical direction of the rectangular region, and a length in the lateral direction of the rectangular region, and a specific format can be modified in various manners.

In a case where the annotation is the information that identifies the rectangular region, the annotation image is information in which the annotation composed of the four values is associated with the endoscope image. In this case, the user such as the doctor performs input to designate the rectangular region using an operation section on the endoscope image displayed on the display section. The user, for example, uses a pointing device such as a mouse and a touch panel to set the rectangular region. Note that a specific input method is not limited thereto.

Additionally, the annotation may be information that identifies a specific shape, in addition to a position of the region of interest. The position and the shape are hereinafter collectively referred to as a position and shape. For example, as illustrated in FIG. 8C, the annotation is mask data indicating the position and shape of the region of interest. For example, the mask data mentioned herein includes the number of pixels that is identical to that of the endoscope image, and is binary image data in which a pixel corresponding to the region of interest is set as a first value and a pixel outside the region of interest is set as a second value. For example, the user such as the doctor performs input to designate a contour of the region of interest using the pointing device and input to fill the inside of the contour to perform annotation. The annotation image in this case is information in which the endoscope image is associated with the mask data.

Usage of the annotation indicating the position and shape enables identification of a specific shape of the region of interest, for example, a degree of spread of a lesion. Hence, usage of the trained model generated with the annotation image including the annotation enables appropriate support for the doctor's diagnosis and treatment. For example, when the doctor resects the lesion, setting of a resection region becomes easier. However, in a case of providing annotation data that identifies the position and shape, a burden on the user is heavier than a case of providing an annotation that is the above-mentioned rectangular region. For example, there is also a case where determination on where the lesion starts and ends on the endoscope image is divided depending on a doctor.

In an endoscopic surgery or the like, there is a case where a target object whose clear position and shape is not displayed in an image has to be identified. For example, an assumable state is a state where a procedure is taken with a predetermined landmark as a guide in the endoscopic surgery, but the position and shape of the landmark is not clearly displayed in the image. The landmark mentioned herein is, for example, the common bile duct, the cystic duct, the Rouviere's sulcus, or the like in cholecystectomy through laparoscopy. An image of the common bile duct or the cystic duct is captured in a state of being covered with another organ or tissues, and thus is not displayed in the image. Since the Rouviere's sulcus gradually disappears toward its end, a boundary of the Rouviere's sulcus is ambiguous. In this case, there is a possibility that a result of determination on the position and shape of the region of interest is significantly different depending on a doctor, and thus a burden on a worker in annotation becomes extremely heavy. Note that the region of interest may be of a plurality of types as described herein. In a case of the above-mentioned example, three types of regions of interest composed of the common bile duct, the cystic duct, and the Rouviere's sulcus are set. In this case, information that identifies not only the position of the region of interest, but also a type of the region of interest, for example, a classification label or the like, is provided in annotation. For example, in the annotation image, three channels of mask data composed of mask data indicating the common bile duct, mask data indicating the cystic duct, and mask data indicating the Rouviere's sulcus are provided, and each channel and the type of the region of interest are associated with each other.

As described above, various forms can be assumed as a specific form of the annotation, and a burden on the worker is different depending on a form. Additionally, a burden on the worker also changes depending on how an image of the region of interest is captured in the endoscope image. But in any case, a burden of performing work of providing an enormous number of endoscope images with annotations is extremely heavy. The method in accordance with the present embodiment for executing the learning using the annotation image within a hospital and making the generated trained model available is advantageous in motivating execution of work with a heavy burden.

2.3 Machine Learning

Subsequently, details of the machine learning are described. The following description is given of the machine learning using the neural network, but the method in accordance with the present embodiment is not limited thereto. In the present embodiment, for example, machine learning using another model such as a support vector machine (SVM) may be performed, and machine learning using a method that has developed from various methods such as the neural network and the SVM may be performed.

Figure 9A:
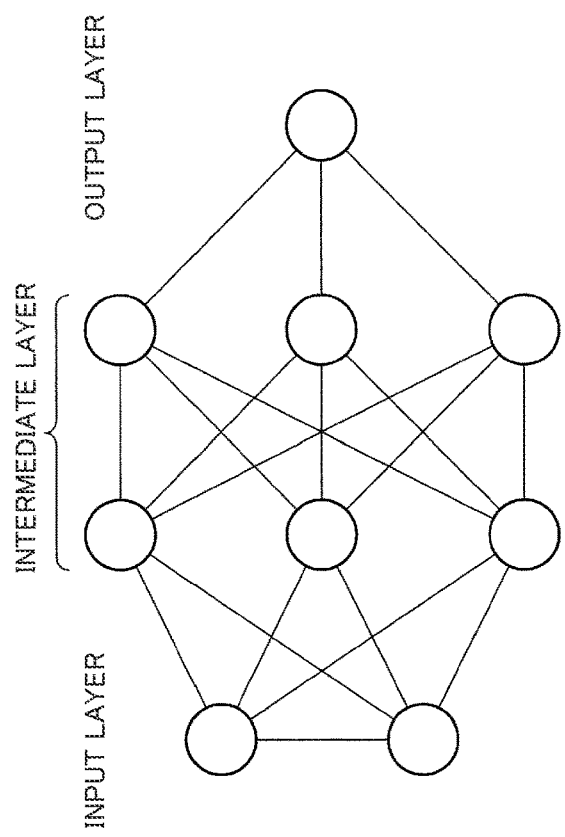
FIGS. 9A and 9B are diagrams for describing a neural network.

FIG. 9A is a schematic diagram for describing the neural network. The neural network includes an input layer taking input data, an intermediate layer executing calculation based on an output from the input layer, and an output layer outputting data based on an output from the intermediate layer. While FIG. 9A exemplifies a network having the intermediate layer composed of two layers, the intermediate layer may be composed of one layer, or three or more layers.

In addition, the number of nodes (neurons) included in each layer is not limited to that in the example of FIG. 9A, and can be modified in various manners. Note that in consideration of accuracy, it is preferable to use deep learning using a multi-layer neural network for the learning in accordance with the present embodiment. The multi-layer mentioned herein means four or more layers in a more limited sense.

As illustrated in FIG. 9A, a node included in a given layer is connected to a node in an adjacent layer. A weight coefficient is assigned between connected nodes. Each node multiplies an output from a node in a former stage by the weight coefficient and obtains a total value of results of multiplication. Furthermore, each node adds a bias to the total value and applies an activation function to a result of addition to obtain an output from the node. This processing is sequentially executed from the input layer to the output layer, whereby an output from the neural network is obtained. Note that as the activation function, various functions such as a sigmoid function and a rectified linear unit (ReLU) function are known, and a wide range of these functions can be applied in the present embodiment.

Learning in the neural network is processing of determining an appropriate weight coefficient (including a bias). Specifically, the learning processor 101 inputs input data out of training data to the neural network and performs calculation in a forward direction using the weight coefficient at this time to obtain an output. The learning processor 101 performs calculation to obtain an error function based on the output and a correct answer label out of the training data. The learning processor 101 updates the weight coefficient to make the error function smaller. In updating the weight coefficient, for example, backpropagation to update the weight coefficient from the output layer to the input layer can be utilized.

Figure 9B:

In addition, the processor 100 may use the annotation image to generate the trained model having undergone machine learning in a convolutional neural network (CNN). FIG. 9B is a schematic diagram for describing the CNN. The CNN includes a convolution layer that performs convolution calculation and a pooling layer. The convolution layer is a layer that performs filter processing. The pooling layer is a layer that reduces a size in a vertical direction and a size in a lateral direction to perform pooling calculation. In an example illustrated in FIG. 9B, the CNN is a network that causes the convolution layer and the pooling layer to each perform calculation a plurality of times, thereafter causes a fully connected layer to perform calculation, and thereby obtain an output. The fully connected layer is a layer that performs calculation processing in a case where all nodes included in the former layer are image-formed to corresponding nodes in the given layer, and the calculation processing corresponds to calculation in each layer described above with reference to FIG. 9A. Note that the calculation processing with the activation function is omitted in FIG. 9B.

In a case where the annotation illustrated in FIG. 8B is provided, the trained model, for example, sets a plurality of windows on the inference endoscope image serving as the input, performs processing of identifying an object within each window, and thereby detects the rectangular region indicating the region of interest. In this case, the output from the fully image-formed layer serves as information indicating a result of identifying whether or not the object on each window is the region of interest.

Additionally, in a case where an annotation illustrated in FIG. 8C is provided, an output from the trained model is, for example, image data that is identical in size to the endoscope image serving as the input. In this case, for example, in substitution for the fully image-formed layer in FIG. 9B, an upsampling layer that enlarges an image size, or the convolution layer is added. In a case where the output layer is a known softmax layer, each pixel of an output image is a numeric value data of not less than 0 and not more than 1 indicating a probability that the pixel is the region of interest.

In addition, the specific configuration of the CNN can be modified in various manners, such as the convolution layer composed of three or more layers. The weight coefficient in the convolution layer in the CNN is a filter parameter. That is, the learning in the CNN includes learning of a filter used for the convolution calculation.

In a case where the CNN is used, a procedure of processing is similar to that illustrated in FIG. 9A. That is, the learning processor 101 performs filter processing or pooling calculation on the endoscope image as the input using filter characteristics at that time to obtain the output. The learning processor 101 calculates the error function based on the output and the correct answer label corresponding to the annotation, and updates the weight coefficient including the filter characteristics to make the error function smaller. For example, the backpropagation can be utilized also when the weight coefficient of the CNN is updated.

Furthermore, processing of imitation learning may be added. In the imitation learning, a configuration to perform learning to be able to trace an identical operation based on endoscope operation data (operation log or the like) of a doctor of the learning hospital may be employed.

Additionally, processing of reinforcement learning may be added. In the reinforcement learning, a configuration to sequentially learn an operation optimized for a specific purpose (detection of a lesion or the like) may be employed.

2. 4 Learning Support

In recent years, various kinds of models used for the machine learning have been known. The model mentioned herein is an algorithm for obtaining output data from the neural network based on input data, and corresponds to a specific structure of the neural network. The structure of the neural network represents, for example, a filter size in the convolution layer in the CNN, a degree of reduction of an image size in the pooling layer, the number of layers, and the like. Information obtained in a given layer may be utilized for calculation in another non-adjacent layer depending on a model, and the model also holds information that identifies contents of such processing. As the model, various kinds of models, such as You Only Look Once (YOLO), a residual neural network (ResNet), and an AlexNet, have been disclosed.

In addition, as an execution environment for these models, various kinds of frameworks have also been known. The framework is a development environment for performing learning in accordance with the model, and includes, for example, a library that defines processing used for a general purpose in the machine learning.

A user who performs the machine learning combines a processor with high computing power, the framework, the model, and the annotation image serving as the training data to generate the trained model used for the processing of detecting the region of interest. Since the endoscope image serves as a processing target in the present embodiment, a GPU with high image processing performance is preferable for the processor (learning processor 101).

Note that there is compatibility between the framework and the model. There is a case where a combination of a first model and a first framework operates normally, but a combination of the first model and a second framework does not operate or decreases in performance. In addition, there is a case where even an identical framework behaves differently depending on a version. For example, the above-mentioned first framework may be a version 1 of a given framework, and the above-mentioned second framework may be a version 2 of the identical framework. Compatibility of the model with the framework is also different depending on a version.

While the description has been given of compatibility between the model and the framework, there is also compatibility with the learning processor 101 (GPU), and it is important to appropriately combine the model, the framework, and the learning processor 101. In consideration of the above points, even in a case where the framework and the model are utilized, it is not easy for a user who does not have expert knowledge regarding the machine learning to perform the machine learning appropriately.

To address this, in the present embodiment, the learning hospital may be provided with a container from the manufacturer of the endoscope system 120. The container mentioned herein includes the model and the framework. The manufacturer of the endoscope system has experience in the machine learning using the endoscope image, and thus has knowledge about a combination of the model and the framework that exerts high performance.

Figure 10:
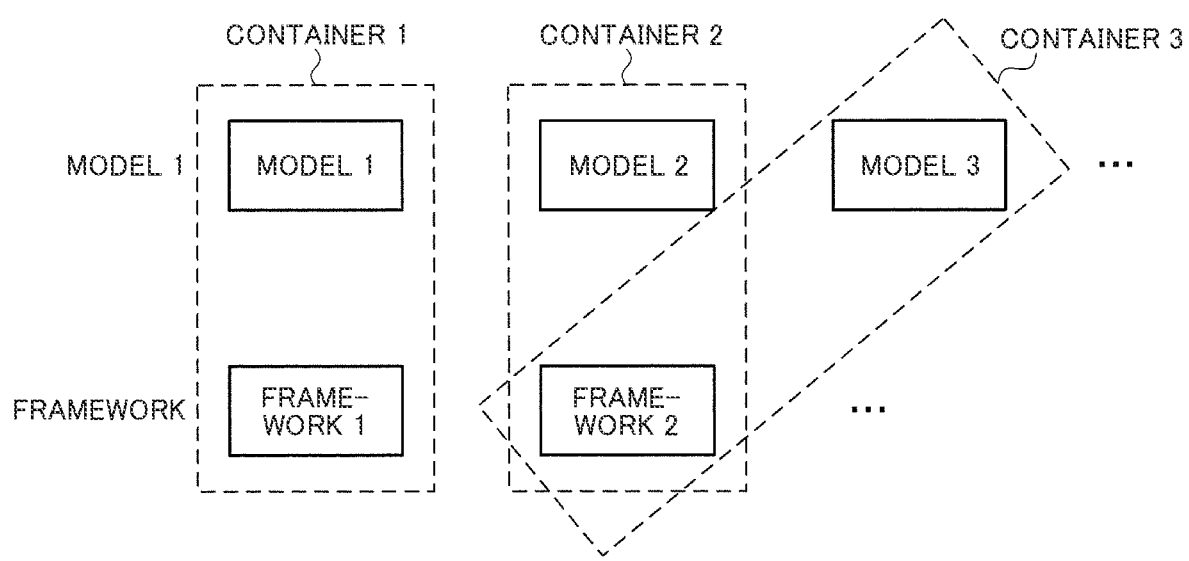
FIG. 10 is a diagram for describing a container in accordance with the present embodiment.

FIG. 10 is a diagram for describing the container in accordance with the present embodiment. In an example in FIG. 10, it is understood that a combination of a model 1 and a framework 1, a combination of a model 2 and a framework 2, and a combination of a model 3 and the framework 2 have good compatibility. On the other hand, it is understood that a combination of the model 1 and the framework 2 or the like, which is not illustrated, decreases in performance. Thus, the manufacturer provides the hospital with a system capable of utilizing these three containers. Specifically, the manufacturer of the endoscope system provides the hospital with, for example, a system including the learning processor 101, the frameworks 1 and 2, and the models 1 to 3. Based on the above assumption, the manufacturer makes the machine learning implemented by the three combinations easily executable.

For example, the manufacturer may provide a program for performing machine learning in accordance with the model 1 in the framework 1. The program mentioned herein is, for example, source codes described in a programming language that can be utilized in the framework 1, utilizing a library provided by the framework 1. In this case, the user makes parameter setting on the program, and can thereby execute the machine learning. The same applies to the other containers.

As described above, the processor 100 may use any of a plurality of containers to perform the machine learning. The container includes the model serving as the algorithm used for the machine learning and the framework serving as the execution environment for performing the machine learning in accordance with the model. This prevents selection of a model and a framework having poor compatibility, and thereby enables appropriate execution of the machine learning.

However, although a combination of the model and the framework to be provided as the container has a potential to exert high performance, whether or not the combination actually exerts high performance depends on a type of the endoscope image serving as the input. For example, an optimal container is different depending on which part is captured as the endoscope image, what kind of a subject serves as a target of the region of interest, or the like. That is, even if the container provided by the manufacturer is used as it is, desired performance is not exerted depending on an endoscope image.

To address this, in the learning-support system in accordance with the present embodiment, the support processor 400 may instruct selection of a container to support the machine learning. For example, the support processor 400 acquires information regarding the endoscope image from the processor 100. The support processor 400 then identifies an appropriate container from a plurality of containers based on the endoscope image, and transmits an instruction for using the container to the processor 100. This enables instruction for usage of the container in accordance with the endoscope image, and thereby enables execution of appropriate machine learning. Note that the learning processor 101 is only required to select a container instructed by the manufacturer. The instruction from the manufacturer may be given with a phone or an e-mail and a selection operation may be performed by a doctor or the like of the learning hospital.

Alternatively, the support processor 400 may give an instruction for setting a parameter included in the model to support the machine learning. The parameter mentioned herein is different from the weight coefficient that can be set by the machine learning, and is a parameter that needs be set by the user.

The parameter is, for example, a learning rate, which is a parameter that determines an amount of change in the weight coefficient. It is known that the learning rate is preferably changed in accordance with progress of the machine learning, and various kinds of optimization methods, such as Momentum, adaptive gradient (AdaGrad), and adaptive moment estimation (Adam), are known. The instruction for setting the learning rate may be an instruction for selecting any of the publicly known optimization methods, or an instruction for designating the learning rate individually.

The number of intermediate layers and a filter size can be changed depending on a model. In this case, the support processor 400 may set them as parameters. Additionally, the support processor 400 may set the above-mentioned activation function as a parameter. Besides these, in the neural network, a regularization coefficient such as weight decay and a parameter such as a dropout rate is known, and the support processor 400 may give an instruction for setting these parameters.

While these parameters are known to affect a speed until convergence and accuracy of the generated trained model, it is extremely difficult to set an appropriate value. Supporting the parameter setting with the support processor 400 allows the user such as the doctor to easily execute the machine learning.

Note that in selecting the container and making the parameter setting, the support processor 400 may perform processing of displaying the endoscope image and the annotation image on the display section included in the fourth network NW4. This allows a person in charge in the manufacturer to confirm image data used for the machine learning and thereafter give an appropriate instruction. However, as described above, in consideration of appropriate management of highly confidential data, the endoscope image and the annotation image in the fourth network NW4 need to be in a form in which secondary usage thereof is not permitted.

3. Selection of Trained Model and Inference Processing Using Trained Model

Figure 11:
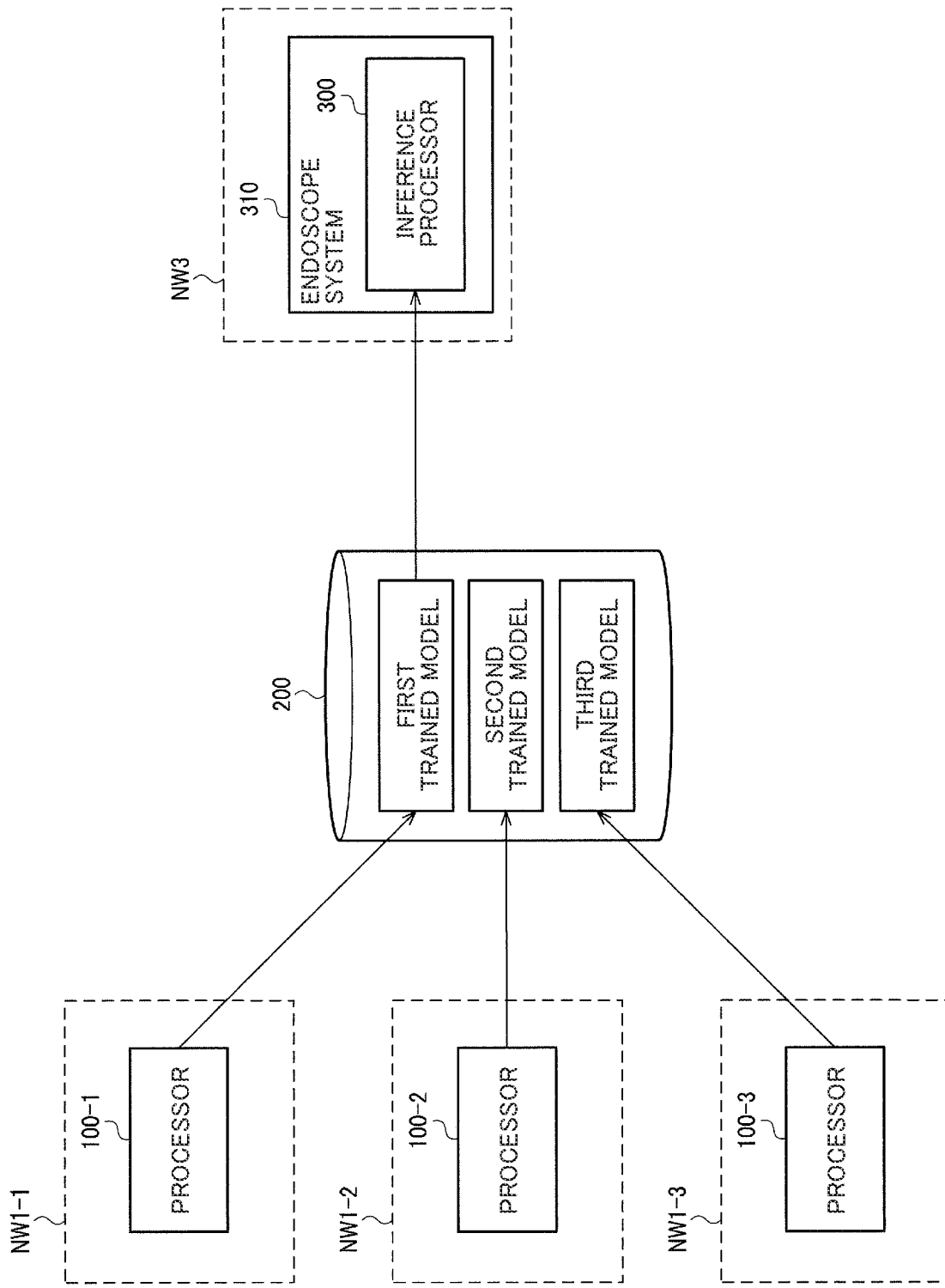
FIG. 11 is a diagram for describing selection and downloading of a trained model.

FIG. 11 is a diagram for describing uploading and downloading of the trained model. As illustrated in FIG. 11, the server system 200 may store a plurality of trained models. For example, as illustrated in FIG. 11, there may be a plurality of learning hospitals. In FIG. 11, there are three learning hospitals, where respective processors 100-1 to 100-3 serving as nodes constituting respective intra-hospital networks NW1-1 to NW 1-3 generate respective trained models 1 to 3. The server system 200 stores three trained models. Note that the number of learning hospitals is not limited to three. Alternatively, a plurality of trained models may be generated in one learning hospital.

In the plurality of trained models mentioned herein, image-capturing conditions for endoscope images used for the machine learning are different. The image-capturing conditions mentioned herein are conditions such as a part serving as an observation target and the region of interest serving as a detection target. In a case where the trained model is utilized in the inference hospital, it is preferable that an image-capturing condition for the inference endoscope image in the inference hospital and an image-capturing condition at the time of learning be identical. For example, in a case where an attempt to detect epithelial cancer from the gastric mucosa is made in the inference hospital, a trained model that should be used is the one having undergone the machine learning using an annotation image in which a region corresponding to the epithelial cancer is provided with an annotation on an endoscope image, which is a captured image of the stomach. For example, in a case of using a trained model having undergone the machine learning using an annotation image in which a region corresponding to, for example, a polyp of the large intestine is provided with an annotation, detection accuracy decreases.

Hence, the inference processor 300 selects a trained model used for the detection processing from a plurality of trained models, and downloads the selected trained model. This enables execution of the inference processing using an appropriate trained model in the inference hospital. That is, the server system 200 in accordance with the present embodiment is a library that accumulates various kinds of trained models having different characteristics, and the inference hospital as a user selects a trained model depending on its own intended use from the library.

Note that to select an appropriate trained model on the inference hospital side, what kind of characteristics each trained model stored in the server system 200 has needs to be known. Hence, the processor 100 in the learning hospital generates compatibility information indicating compatibility between the endoscope system 310 that captures the inference endoscope image and the trained model, associates the trained model and the compatibility information with each other, and uploads the trained model and the compatibility information to the server system 200. The compatibility information associated with the trained model is information indicating to what kind of the endoscope system 310 the trained model is adapted. The adaptation mentioned herein indicates that the inference processing utilizing the trained model can be executed with sufficiently high accuracy.

For example, the compatibility information may be information indicating the manufacturer of the endoscope system, or information indicating a model number of a product. If the manufacturer and the model number are identified, information regarding an imaging optical system, such as a lens configuration, an aperture value range, a zoom magnification range, and a size of an image sensor, is determined. Since characteristics of the endoscope image to be captured is determined based on the information, it is possible to determine whether or not the trained model is adapted to the endoscope system 310 of the inference hospital. Note that in a case where the insertion section 10 (scope) of an interchangeable type is used, the compatibility information may include information regarding a model number that identifies the insertion section 10 or other information.

The compatibility information may include information regarding illumination light emitted when the endoscope image is captured. For example, in the endoscope system, there is a widely known method of emitting special light having a wavelength band that is different from that of white light to capture a special light image. The special light image is an NBI image captured by emission of green narrow band light and blue narrow band light. In a case where the machine learning is performed with the NBI image serving as an input of a model, it is necessary to input the NBI image to the trained model also in the inference processing. Hence, the processor 100, for example, provides the trained model with the compatibility information indicating that the trained model is adapted to the endoscope system 310 capable of capturing the NBI image, and uploads the trained model to the server system 200.

In addition, the compatibility information may be information regarding a part serving as an observation target and the region of interest serving as a detection target. As described above, targeting the region of interest of an identical part and an identical type can increase accuracy of the inference processing using the trained model.

Alternatively, the compatibility information may be information regarding anamnesis of a patient who is a target of endoscopic diagnosis, or other information. For example, it is known that elimination of *Helicobacter pylori* decreases an occurrence rate of stomach cancer. Hence, it is assumed that a patient who has not undergone elimination of the *Helicobacter pylori* and a patient who has undergone elimination of *Helicobacter pylori* have different tendencies when an image of the gastric mucosa is captured. The trained model is preferably divided into a model to be applied to the patient who has undergone elimination of the *Helicobacter pylori* and a model to be applied to the patient who has not undergone elimination of the *Helicobacter pylori*. The compatibility information in this case is information indicating presence/absence of elimination of the *Helicobacter pylori*.

As described above, various kinds of information, such as the manufacturer, the model number, the part serving as the target of image-capturing, the type of the region of interest, the number of illumination light, the wavelength band of illumination light, and the anamnesis of the patient, can be used as the compatibility information. A user in the inference hospital compares between the compatibility information provided to the trained model and information regarding the configuration of the endoscope system 310 of the inference hospital, a part whose image is captured, the region of interest serving as a detection target, and a patient serving as a target of image-capturing, and the like, and thereby selects an appropriate trained model.

It is not preferable that whether or not the trained model is adapted to the endoscope system 310 of the inference hospital be determined in an excessively strict manner. In a case of the example of the NBI image, each of green narrow band light and blue narrow band light is light having characteristics of being highly sensitive to hemoglobin. For this reason, a peak wavelength and half-value width of illumination light are only required to be in a range that exerts the characteristics, and can be modified in various manners. That is, wavelength bands and the like of green narrow band light and blue narrow band light in capturing of the endoscope image, and those of green narrow band light and blue narrow band light in capturing of the inference endoscope image need not be strictly matched with each other, and are only required to have similarities to some extent to enable the inference processing with sufficiently high accuracy.

For example, the compatibility information includes not only information regarding green narrow band light and blue narrow band light emitted by the endoscope system 120 in the learning hospital as it is, but also information regarding another light having similar characteristics. Specifically, each of the peak wavelength and the half-value width is represented as a given range of numeric values, instead of one value. This can prevent a range of application of the trained model from being excessively narrowed, and can thereby expedite utilization of the trained model. The same applies to compatibility information other than that regarding a light source, and it is preferable that the compatibility information be expanded to other information having high similarity levels, instead of being limited to information in the learning hospital.

Note that the server system 200 may select an adaptable trained model. For example, the inference processor 300 transmits information such as the configuration of the endoscope system 310 of the inference hospital, the image-capturing condition, and the patient serving as the target of image-capturing to the server system 200. The server system 200 calculates a similarity level between the information transmitted from the inference processor 300 and the compatibility information, and presents a trained model that has the similarity level that is equal to or greater than a given similarity level threshold to the inference processor 300. The inference processor 300 downloads the selected trained model from presented one or more trained models. Note that in this case, the range of application of the trained model may be prevented from being excessively narrowed by adjustment of the similarity level threshold.

Once the trained model to be utilized is determined, the endoscope system 310 of the inference hospital downloads the trained model, and performs the inference processing using the trained model. Note that the trained model is stored in a memory serving as a node that is included in the third network NW3 and not illustrated. The memory mentioned herein is, for example, a memory included in the inference processor 300, and corresponds to the storage section 37 illustrated in FIG. 4. In addition, the memory may be a non-volatile memory, or a volatile memory. Specifically, the inference processor 300 of the endoscope system 310 performs calculation in accordance with the trained model to perform the processing of detecting the region of interest. Note that the trained model is utilized as a program module, which is part of artificial intelligence software.

Calculation in accordance with the trained model in the inference processor 300, that is, calculation for outputting output data based on input data, may be executed by software or hardware. In other words, the convolution calculation or the like in the CNN may be executed by software. Alternatively, the above-mentioned calculation may be executed by a circuit device such as a field-programmable gate array (FPGA) circuit. Alternatively, the above-mentioned calculation may be executed by software and hardware in combination. In this manner, operations of the inference processor 300 in accordance with an instruction from the trained model can be implemented in various manners. For example, the trained model includes an inference algorithm, and a parameter used for the inference algorithm. The inference algorithm is an algorithm that performs product-sum calculation, the convolution calculation, or the like based on input data, and corresponds to the above-mentioned model. The parameter is a parameter acquired by the learning processing, and is, for example, the weight coefficient in the neural network. In this case, both the inference algorithm and the parameter are stored in the memory, and the inference processor 300 may read out the inference algorithm and the parameter to perform the inference processing with software. Alternatively, the inference algorithm may be implemented by an FPGA circuit or the like.

Figure 12:
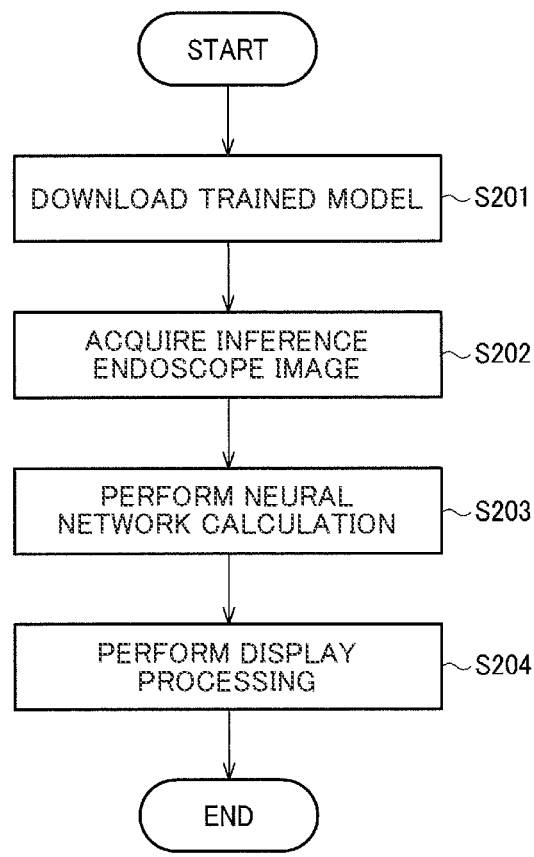
FIG. 12 is a flowchart describing inference processing.

FIG. 12 is a flowchart describing the inference processing in the inference processor 300. Before the start of the specific inference processing, in step S201, the inference processor 300 downloads a trained model that suits intended use from the server system 200.

In S202, the inference processor 300 controls the light source device or the image sensor in the endoscope system 310 to acquire the inference endoscope image. In step S203, the inference processor 300 operates in accordance with an instruction from the downloaded trained model to perform processing of detecting the region of interest from the inference endoscope image. Specifically, the inference processor 300 performs neural network calculation with the inference endoscope image serving as input data. Furthermore, in S204, the inference processor 300 performs processing of displaying a detection result. For example, the inference processor 300 performs highlighting processing to increase visibility of the detected region of interest on the original inference endoscope image, and outputs a processing result on the display section.

Note that the trained model in accordance with the present disclosure may include not only a model generated in the learning hospital as it is, but also a derived model generated based on the model.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. A learning support system comprising:
a storage configured to store an endoscope image generated in a first network and an annotation image generated in the first network, the annotation image having undergone annotation on a region of interest in the endoscope image;
a processor including hardware;
a server system configured to perform communications with the processor, and have a trained model uploaded thereto by the processor; and
an inference processor including hardware,
wherein:
the processor is configured to acquire the annotation image from the storage, use the annotation image to perform machine learning, and generate the trained model;
the storage and the processor each serve as a node constituting the first network;
the server system serves as a node constituting a second network;
the first network is an intra-hospital network;
the second network is an extra-hospital network;
the inference processor is configured to perform communications with the server system to download the trained model, and perform detection processing of detecting the region of interest from an inference endoscope image based on the trained model;
the inference endoscope image is an image serving as an input of inference processing using the trained model;
the inference processor is configured to serve as a node constituting a third network; and
the third network is a network of an inference hospital that executes the inference processing.

2. The learning support system as defined in claim 1, wherein the intra-hospital network is a more secure network, as compared with the extra-hospital network, for the endoscope image and the annotation image.

3. The learning support system as defined in claim 2, wherein the intra-hospital network restricts accessible Internet Protocol (IP) addresses.

4. The learning support system as defined in claim 1, wherein the intra-hospital network is an intranet, and the extra-hospital network is the Internet.

5. The learning support system as defined in claim 4, wherein:
the intra-hospital network includes a first intranet and a second intranet; and
the node in the first intranet and the node in the second intranet are nodes constituting a block chain network, or the first intranet and the second intranet constitute a virtual private network (VPN).

6. The learning support system as defined in claim 1, wherein the processor is configured to use the annotation image to generate the trained model having undergone the machine learning in a convolutional neural network (CNN).

7. The learning support system as defined in claim 1, wherein:
the processor is configured to generate compatibility information indicating compatibility between an endoscope system that captures an image of the inference endoscope image and the trained model, associate the trained model and the compatibility information with each other, and upload the trained model and the compatibility information to the server system.

8. The learning support system as defined in claim 1, wherein;
the server system is configured to store a plurality of the trained models; and
the inference processor is configured to select the trained model used for the detection processing from the plurality of the trained models, and download the selected trained model.

9. The learning support system as defined in claim 1, further comprising a support processor including hardware, the support processor being configured to perform communications with the processor to support the machine learning, wherein:
  the support processor is configured to serve as a node constituting a fourth network; and
  the fourth network is a network of a manufacturer of an endoscope system that generates the endoscope image.

10. The learning support system as defined in claim 9, wherein:
  the processor is configured to use any of a plurality of containers to perform the machine learning;
  the container includes a model serving as an algorithm used for the machine learning and a framework serving as an execution environment for the machine learning in accordance with the model; and
  the support processor is configured to give an instruction for selection of the containers to support the machine learning.

11. The learning support system as defined in claim 10, wherein the support processor is configured to give an instruction for setting a parameter included in the model to support the machine learning.

12. A learning support system comprising:
  a storage configured to store an endoscope image generated in a first network and an annotation image generated in the first network, the annotation image having undergone annotation on a region of interest in the endoscope image;
  a processor including hardware; and
  an inference processor including hardware,
  wherein:
    the processor is configured to acquire the annotation image from the storage, use the annotation image to perform machine learning, generate a trained model, and upload the trained model to a server system;
    the storage and the processor each serve as a node constituting the first network;
    the server system serves as a node constituting a second network;
    the first network is an intra-hospital network;
    the second network is an extra-hospital network;
    the inference processor is configured to perform communications with the server system to download the trained model, and perform detection processing of detecting the region of interest from an inference endoscope image based on the trained model;
    the inference endoscope image is an image serving as an input of inference processing using the trained model,
    the inference processor is configured to serve as a node constituting a third network, and
    the third network is a network of an inference hospital that executes the inference processing.

13. A learning support system comprising
  a support processor including hardware and configured to perform communications with a processor to support machine learning; and
  an inference processor including hardware,
  wherein:
    the processor acquires an annotation image, from a storage that stores an endoscope image generated in a first network and the annotation image generated in the first network, the annotation image having undergone annotation on a region of interest in the endoscope image, uses the annotation image to perform the machine learning, generates a trained model, and uploads the generated trained model to a server system;
    the support processor selects a container including a model serving as an algorithm used for the machine learning and a framework serving as an execution environment for the machine learning in accordance with the model to support the machine learning;
    the storage and the processor each serve as a node constituting the first network;
    the server system serves as a node constituting a second network;
    the inference processor is configured to perform communications with the server system to download the trained model, and perform detection processing of detecting the region of interest from an inference endoscope image based on the trained model;
    the inference endoscope image is an image serving as an input of inference processing using the trained model;
    the inference processor is configured to serve as a node constituting a third network;
    the third network is a network of an inference hospital that executes the inference processing;
    the support processor serves as a node constituting a fourth network;
    the first network is an intra-hospital network;
    the second network is an extra-hospital network; and
    the fourth network is a network of a manufacturer of an endoscope system that generates the endoscope image.

14. A learning support method comprising:
  storing, in a storage, an endoscope image generated in a first network and an annotation image generated in the first network, the annotation image having undergone annotation on a region of interest in the endoscope image;
  using, by a processor including hardware, the annotation image to perform machine learning, and generating, by the processor, a trained model;
  uploading, by the processor, the generated trained model to a server system that serves as a node constituting a second network
  downloading, by an inference processor including hardware performing communications with the server system, the trained model, and performing, by the inference processor, detection processing of detecting the region of interest from an inference endoscope image based on the trained model,
  wherein:
    each of the storing of the annotation image and the generation of the trained model is executed in the first network;
    the first network is an intra-hospital network;
    the second network is an extra-hospital network;
    the inference endoscope image is an image serving as an input of inference processing using the trained model,
    the inference processor is configured to serve as a node constituting a third network; and
    the third network is a network of an inference hospital that executes the inference processing.

* * * * *